(12) United States Patent
Gore et al.

(10) Patent No.: US 10,279,005 B2
(45) Date of Patent: May 7, 2019

(54) STABILIZED OMEGA-3 OPHTHALMIC COMPOSITIONS

(71) Applicant: Allergan, Inc., Irvine, CA (US)

(72) Inventors: Anuradha V. Gore, Aliso Viejo, CA (US); Jaya Giyanani, Irvine, CA (US); Sukhon Likitlersuang, Corona, CA (US)

(73) Assignee: ALLERGAN, INC., Irvine, CA (US)

(*) Notice: Subject to any disclaimer, the term of this patent is extended or adjusted under 35 U.S.C. 154(b) by 323 days.

(21) Appl. No.: 14/949,352

(22) Filed: Nov. 23, 2015

(65) Prior Publication Data

US 2016/0143977 A1    May 26, 2016

Related U.S. Application Data

(60) Provisional application No. 62/083,980, filed on Nov. 25, 2014.

(51) Int. Cl.
| | |
|---|---|
| A61K 36/55 | (2006.01) |
| A61K 9/00 | (2006.01) |
| A61K 31/085 | (2006.01) |
| A61K 31/05 | (2006.01) |

(52) U.S. Cl.
CPC ............ *A61K 36/55* (2013.01); *A61K 9/0048* (2013.01); *A61K 31/05* (2013.01); *A61K 31/085* (2013.01)

(58) Field of Classification Search
None
See application file for complete search history.

(56) References Cited

U.S. PATENT DOCUMENTS

| | | | |
|---|---|---|---|
| 4,201,706 A | 5/1980 | Trager et al. | |
| 4,649,047 A | 3/1987 | Kaswan | |
| 4,839,342 A | 6/1989 | Kaswan | |
| 5,145,871 A | 9/1992 | Cavazza | |
| 5,411,952 A | 5/1995 | Kaswan | |
| 5,432,199 A | 7/1995 | Cavazza | |
| 5,474,979 A | 12/1995 | Ding et al. | |
| 5,527,831 A | 6/1996 | Franz | |
| 5,827,512 A | 10/1998 | Gleich | |
| 5,981,607 A | 11/1999 | Ding et al. | |
| 6,156,293 A | 12/2000 | Jutila et al. | |
| 6,193,957 B1 | 2/2001 | Ahmed | |
| 6,228,392 B1 | 5/2001 | Morcos et al. | |
| 6,365,622 B1 | 4/2002 | Cavazza | |
| 6,555,526 B2 | 4/2003 | Matsuo et al. | |
| 6,585,987 B1 | 7/2003 | Fransoni | |
| 6,635,654 B1 | 10/2003 | Chang et al. | |
| 7,045,121 B2 | 5/2006 | Chang et al. | |
| 8,496,976 B2 | 7/2013 | Gore et al. | |
| 8,569,367 B2 | 10/2013 | Vehige et al. | |
| 8,679,554 B2 | 3/2014 | Gore et al. | |
| 8,957,048 B2 | 2/2015 | Vehige et al. | |
| 9,821,020 B2* | 11/2017 | Gore ...................... | A61K 36/47 |
| 2002/0071874 A1 | 6/2002 | Olejnik et al. | |
| 2004/0137079 A1 | 7/2004 | Cook et al. | |
| 2004/0192647 A1 | 9/2004 | Babizhayev | |
| 2005/0009836 A1 | 1/2005 | Laskar et al. | |
| 2006/0035842 A1 | 2/2006 | Tsuzuki et al. | |
| 2006/0106104 A1 | 5/2006 | Vehige | |
| 2006/0251685 A1 | 11/2006 | Yu et al. | |
| 2007/0265341 A1 | 11/2007 | Dana et al. | |
| 2008/0026991 A1 | 1/2008 | Rabinovicj-Guilatti et al. | |
| 2008/0070834 A1 | 3/2008 | Chang et al. | |
| 2008/0153909 A1 | 6/2008 | Dana et al. | |
| 2008/0207495 A1 | 8/2008 | Graham et al. | |
| 2010/0184664 A1 | 7/2010 | Simmons et al. | |
| 2010/0305045 A1 | 12/2010 | Yu | |
| 2014/0141106 A1 | 5/2014 | Gore et al. | |

FOREIGN PATENT DOCUMENTS

| | | |
|---|---|---|
| EP | 0028110 | 5/1981 |
| EP | 0436726 | 7/1990 |
| EP | 0778021 | 6/1997 |
| EP | 1044678 | 10/2000 |
| GB | 2224205 | 5/1990 |
| JP | S56104814 | 8/1981 |
| JP | 2763400 | 3/1998 |
| JP | 2010-036255 | 2/2010 |
| WO | 1998-041208 | 9/1998 |
| WO | 2002-038161 | 5/2002 |
| WO | 2003-051332 | 6/2003 |
| WO | 2004-084877 | 7/2004 |
| WO | 2008-027341 | 3/2008 |
| WO | 2008-106228 | 9/2008 |
| WO | 2010-106571 | 9/2010 |
| WO | 2010-047927 | 12/2010 |
| WO | 2010-141648 | 12/2010 |
| WO | 2013-052760 | 4/2013 |

OTHER PUBLICATIONS

Nettune, Gregory R. et al., Post-LASIK Tear Dysfunction and Dysesthesia, The Ocular Surface 2010, 8: (8) 135-145.
Yu, Edward Y.W. et al., Effect of Laser in Situ Keratomileusis on Tear Stability, Ophthalmology 2000, 107: 2131-2135 (8).
Cakiner-Egilmez, T., Omega 3 Fatty Acids and the Eye, Insight 2004, 32: 20-28 (4).
Hom, Milton M. et al., Understanding Emulsion Eye Drop Technology, Review of Optometry 2008, 5 pages.
Jumaa, Muhannad et al., Mixture experiments with the oil phase of parenteral emulsions, European Journal of Pharmaceutics and Biopharmaceutics 1998, 46: 161-167.
Jumaa, Muhannad et al., The effect of oil components and homogenization conditions on the physicochemical properties and stability of parenteral fat emulsions, International Journal of Pharmaceutics 1998, 163: 81-89.

(Continued)

*Primary Examiner* — Susan Hoffman
(74) *Attorney, Agent, or Firm* — Lorenz Siddiqi

(57) ABSTRACT

Stabilized ophthalmic compositions containing omega-3 oils are provided, which are useful as artificial tears and as ophthalmic compositions to diagnose, treat, or prevent keratoconjunctivitis or dry eye syndrome in a human or other mammal.

8 Claims, 3 Drawing Sheets

(56) References Cited

OTHER PUBLICATIONS

Rashid, Saadia et al., Topical Omega-3 and Omega-6 Fatty Acids for Treatment of Dry Eye, Arch. Ophthalmol., 126: 219-225 2008.
Khanal, Santosh et al., Effect of an Oil-In-Water Emulsion on the Tear Physiology of Patients With Mild to Moderate Dry Eye, Cornea 2007, 26: 175-181 (2).
Database WPI Week 191840 Thomson Scientific, London, GB; AN 1981-72752DXP002591551 & JP 56 104814 A (Okanoue K) Aug. 20, 1981 (Aug. 20, 1981).
Vieira, Celme et al., Effect of ricinoleic acid in acute and subchronic experimental models of inflammation, Mediators of Inflammation 2000, 9: 223-228.
Albietz, Julie et al., A Comparison of the Effect of Refresh plus and Bion Tears on Dry Eye Symptoms and Ocular Surface Health in Myopic LASIK Patients, the CLAO Journal, 2002, 96-100, 28(2).
Alfieri, Roberta et al, Compatible Osmolytes Modulate the Response of Porcine Endothelial Cells to Hypertonicity and Protect Them From Apoptosis, J. Physiol., 2002, 499-508, 540.
Barker, Robert et al, Acidic Polyamino Acids Inhibit Human Eosinophil Granule Major Basic Protein Toxicity. Evidence of a Functional Role for ProMBP, J. Clin. Invest., Sep. 1991, 798-805, 88.
Biocompare®: Product Review: Upstate's Beadlyte Human/Mouse Cytokine Detection Kits, Jun. 15, 2004, 3 Pages, Biocompare, Inc.
Brown, Theodore et al, Glossary: Salt, Chemistry: The Central Science, 2006, G-10, 10th Edition.
Burg, Maurice, Molecular Basis of Osmotic Regulation, American Physiological Society, 1995, F983-F996, 268.
Cammarata, Patrick et al, Osmoregulatory Alterations in taurine Uptake by Cultured Human and Bovine lens Epithelial Cells, Invest. Ophthalmol. Vis. Sci., 2002, 425-433, 43.
Gilbard, Jeffrey, Tear Film Osmolarity and Keratoconjunctivitis Sicca, the CLAO Journal, Jul. 1985, 243-250, 11 (3).
Matsuo, Toshihiko et al, Trehalose Eye Drops in the Treatment of Dry Eye Syndrome, Ophthalmology, 2002, 2024-2029, 109.
McGrogan, Michael et al, Isolation of a Complementary DNA Clone Encoding a Precursor to Human Eosinophil Major Basic Protein, J. Exp. Med., Dec. 1988, 2295-2308, 168.
Nakajima, Toshiharu et al, Gene Expression Screening of Human Mast Cells and Eosinophils Using High-Density Oligonucleotide Probe Arrays: Abundant Expression of Major Basic Protein in Mast Cells, Blood, Aug. 2001, 1127-1134, 98 (4).
Peluso, Gianfranco et al, Carnitine: An Osmolyte That Plays a Metabolic Role, Journal of Cellular Biochemistry, 2000, 1-10, 80.
Pessotto, P. et al, The Presence of L-Carnitine in Ocular Tissues of the Rabbit, Journal of Ocular Pharmacology, 1994, 643-651, 10 (4).
Popken-Harris, Pamela et al, Biochemical Properties, Activities, and Presence in Biologic Fluids of Eosinophil Granule Major Basic Protein, J. Allergy Clin. Immunol., 1994, 1282-1289, 94 (6).
Popken-Harris, Pamela et al, Regulation and Processing of a Precursor Form of Eosinophil Granule Major Basic Protein (ProMBP) in Differentiating Eosinophils, Blood, Jul. 1998, 623-631, 92 (2).
Rhyne, P.W. et al, Analysis of Apoptotic Cells Using Beadlyte Suspension Arrays, Biotechniques, Sep. 2003, 624-629 (Abstract), 35 (3).
Shioda, Ryo et al, Osmosensitive Taurine Transporter Expression and Activity in Human Corneal Epithelial Cells, Investigative Ophthalmology & Visual Science, Sep. 2002, 2916-2922, 43 (9).
Voet et al, Transport Across the Mitochondrial Membrane, Biochemistry, 1990, 622.
Patent Cooperation Treaty, International Search Report and Written Opinion, dated Feb. 22, 2013, International Application No. PCT/US2012/068603.
Patent Cooperation Treaty, International Search Report and Written Opinion, dated Feb. 22, 2013, International Application No. PCT/US2012/068615.
Patent Cooperation Treaty, International Search Report and Written Opinion, dated Dec. 3, 2012, International No. Application PCT/US2012/058893.
Patent Cooperation Treaty, International Search Report and Written Opinion, dated Jan. 13, 2011, International Application No. PCT/US2010/037153.
Glossary of Medical Education Terms, Institute of International Medical Education, http://www.iime.org/glossary.htm, accessed in Mar. 2013.
Javadi, Mohammad-Ali et al., Dry Eye Syndrome, J. Ophthalmic. Vis. Res. 2011, 6: 192-198 (3).
International Search Report & Written Opinion dated Jan. 13, 2011 for PCT/US10/37153 filed Jun. 3, 2010 in the name of Allergan, Inc.

\* cited by examiner

STABILIZED OMEGA-3 OPHTHALMIC COMPOSITIONS

CROSS REFERENCE

This application claims the benefit of U.S. Provisional Application Ser. No. 62/083,980 filed on Nov. 25, 2014, the disclosure of which is hereby incorporated in its entirety herein by reference.

FIELD

Provided herein are stabilized ophthalmic compositions containing omega-3 oils. Among other things, the compositions are useful as artificial tears and as ophthalmic compositions to diagnose, treat, or prevent dry eye syndrome or keratoconjunctivitis in a human or other mammal in need of such diagnosis treatment, or prevention.

BACKGROUND

Omega-3 oils are widely noted in the published literature for their beneficial effects on ocular health, and certain omega-3 fatty acids are known to be significant components of the mammalian eye. See, e.g., Insight, October-December; 33(4): 20-5 (2008). A majority of omega-3 oil products are formulated as soft or hard gel capsules filled with omega-3 oil compositions which are intended for oral and systemic delivery of the omega-3 oils. Currently there are no commercial ophthalmic products in US market containing omega-3 oils for ocular surface delivery. Emulsions are typically the preferred dosage form for delivery of oily components to the surface of the eye, in which the oil dispersed in the water phase as droplets typically in the sub-micron range by using surfactants and emulsifiers.

A major hurdle in development of an ophthalmic product containing the omega-3 oils is the chemical stability of the omega-3 components which are susceptible degradation by oxidation and hydrolysis. U.S. Patent Publication Nos. 2007/0265341, 2008/0153909 and 2010/0305045, for example, teach certain omega-3 oil containing compositions, but do not address this stability issue. U.S. 2007/0265341 teaches the use of vitamin E as an antioxidant, but vitamin E is not effective in preserving omega-3 oils as described herein. Thus, there is a need for stable ophthalmic compositions containing omega-3 oils.

SUMMARY

Provided herein are stabilized ophthalmic compositions containing omega-3 oils and one or more antioxidants. Specifically, the antioxidants are selected from butylated hydroxyanisole (BHA) and butylated hydroxytoluene (BHT), alone or in combination. These compositions may be used, among other things, as artificial tears and as ophthalmic compositions to diagnose, treat, or prevent keratoconjunctivitis or dry eye syndrome in a human or other mammal in need of such diagnosis, treatment, or prevention.

DETAILED DESCRIPTION DETAILED DESCRIPTION

Figure 1:
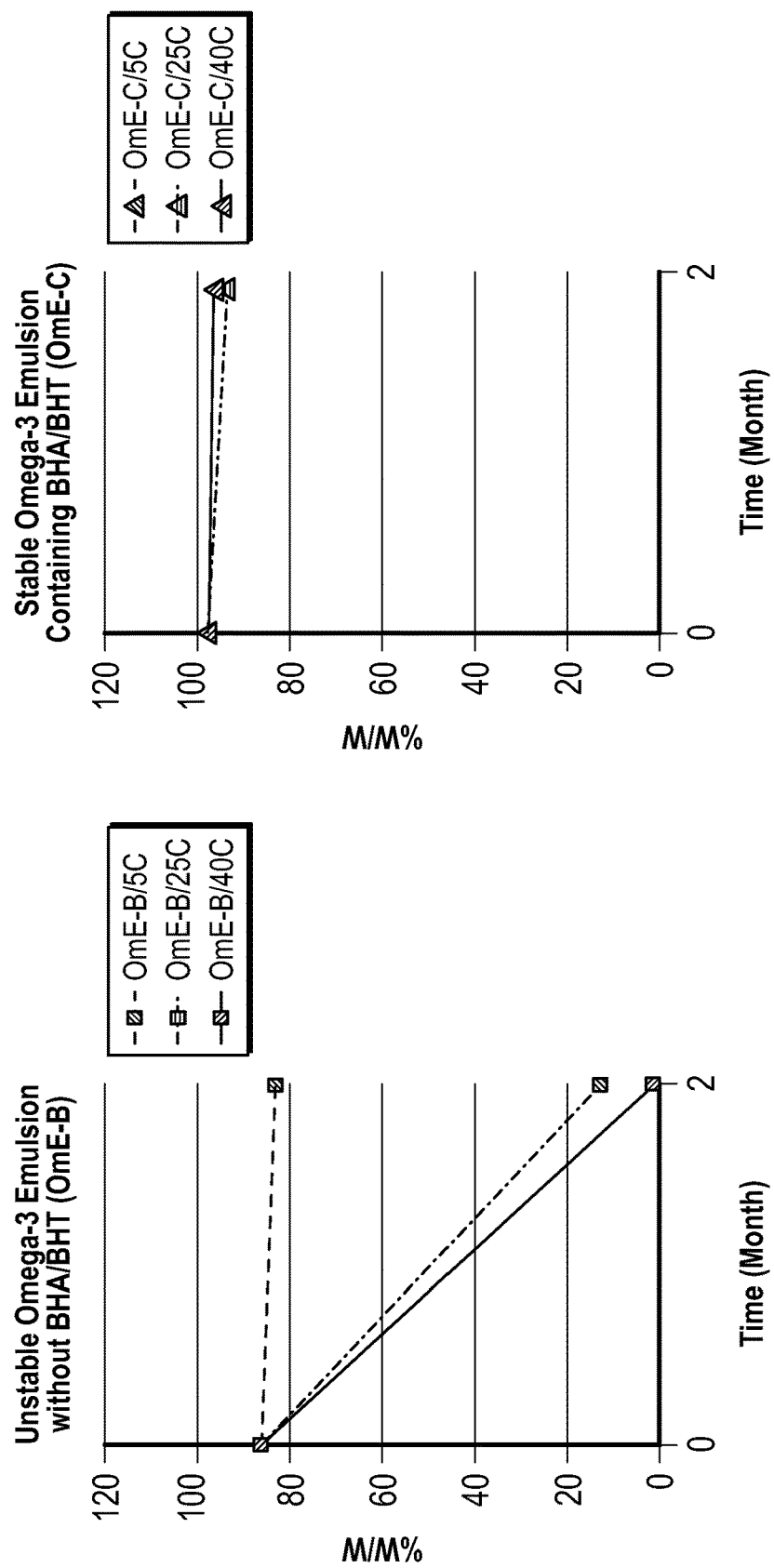
FIG. 1 shows the improved chemical stability of omega-3 oils in emulsions containing BHA and BHT, as compared to emulsions containing omega-3 oil without BHA/BHT.

Provided herein are stabilized ophthalmic compositions containing omega-3 oils and one or more antioxidants. Specifically, the antioxidants are selected from butylated hydroxyanisole (BHA) and butylated hydroxytoluene (BHT), alone or in combination.

Butylated hydroxytoluene (BHT) is also known as butylhydroxytoluene, tert-butylhydroxytoluene, or 2,6-bis(1,1-dimethylethyl)-4-methylphenol. Butylated hydroxyanisole (BHA) is also known as butylhydroxyanisole or tert-butylhydroxyanisole. BHA commonly includes a mixture of 2-tert-butyl-4-hydroxyanisole and 3-tert-butyl-4-hydroxyanisole.

The inventors surprising found that BHA, BHT, or combinations thereof exhibit a unique stabilizing effect on omega-3 oils as compared to other known antioxidants. A variety of ophthalmic compositions were evaluated which contained antioxidants with the intent to prevent the degradation of the omega-3 oil components. A common problem with omega-3 oils is their propensity to degrade and become rancid over time. Surprisingly, many commonly used antioxidants for oils such as ascorbyl palmitate, alpha tocopherol and Vitamin E acetate did not show beneficial effects in protecting the omega-3 components from degradation. Even more surprisingly, in some cases these antioxidants enhanced the degradation rates of the omega-3 oils. Only BHA and BHT were found to have a stabilizing effect on the omega-3 oils.

Utilizing this stabilizing property of BHA and BHT, several novel formulation compositions were developed for omega-3 oil containing ophthalmic emulsions. Emulsion prototypes were designed using a range of excipients including different surfactants, antioxidants and aqueous additives. The physical and chemical stability of these prototype formulations were monitored over 3, 6 and/or 12 months at accelerated and/or long term storage conditions. It was found that emulsions containing BHA and/or BHT were chemically and physically stable for 3, 6 and/or 12 months at accelerated and/or long term storage conditions. The addition of other oil soluble antioxidants, such as Vitamin E acetate, ascorbyl palmitate and alpha-tocopherol led to degradation of omega-3 oil along with a change in physical appearance of the emulsions. Water soluble additives such as EDTA, trehalose and pyruvate did not impact stability for the emulsions. Details of these stability studies are provided in the examples herein.

The compositions provided herein may be used, among other things, as artificial tears and/or as ophthalmic compositions for the treatment of dry eye, or to diagnose, treat, or prevent keratoconjunctivitis or dry eye syndrome in man or other animals. The ophthalmic compositions provided herein may also include one or more therapeutic agents, in addition to one or more omega-3 oils.

In addition to the omega-3 oils and antioxidant selected from BHA, BHT and mixtures thereof, the ophthalmic compositions provided herein may contain other ingredients suitable for ophthalmic use. These compositions are also referred to as ophthalmically acceptable liquids. An ophthalmically acceptable liquid includes a liquid formulated to be tolerable to a patient for topical ophthalmic use. An ophthalmically acceptable liquid may be a solution or an emulsion.

For ophthalmic application, solutions or other forms of compositions/medicaments may be prepared, for example, by using a physiological saline solution as a major vehicle. Ophthalmic solutions or compositions may be maintained at a comfortable pH with an appropriate buffer system. The formulations may also contain conventional, pharmaceutically acceptable preservatives, stabilizers and surfactants.

In some embodiments, the ophthalmic composition provided herein includes a buffer. The buffer may vary, and may include any weak conjugate acid-base pair suitable for maintaining a desirable pH range. Examples include, but are not limited to, acetate buffers, citrate buffers, phosphate buffers, borate buffers, or a combination thereof. Acids or bases may be used to adjust the pH of these formulations as needed. The amount of buffer used may vary. In some embodiments, the buffer may have a concentration in a range of about 1 nM to about 100 mM. The pH of a buffered solution may be increased by the addition of NaOH or another base, or decreased by the addition of HCl or another acid. In some embodiments, the pH of a composition may be about 6.4 to about 7.8; 6.8 to about 7.5; 6.8 to about 7.4; 6.8 to about 7.3; 6.8 to about 7.2; 6.9 to about 7.1; or about 6.8; about 6.9; about 7.0; about 7.1; about 7.2 or about 7.3.

An ophthalmic composition provided herein may include one or more surfactants. The surfactant may vary, and may include any compound that is surface active or can form micelles. A surfactant may be used for assisting in dissolving an excipient or an active agent, dispersing a solid or liquid in a composition, enhancing wetting, modifying drop size, stabilizing an emulsion, or a number of other purposes. Useful surfactants include, but are not limited to, surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated aryl phenols; ethoxylated fatty acids; ethoxylated; fatty esters or oils (animal and vegetable); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated and ethoxylated fatty acids, alcohols, or alkyl phenols; protein-based surfactants; sarcosine derivatives; sorbitan derivatives; sucrose and glucose esters and derivatives. In some embodiments, the surfactant may include polyethylene glycol (15)-hydroxystearate (CAS Number 70142-34-6, available as Solutol HS 15® from BASF), polyoxyethylene-polyoxypropylene block copolymer (CAS No. 9003-11-6, available as Pluronic® F-68 from BASF), polyoxyethylene 40 stearate (POE 40 stearate), polysorbate 80 or polyoxyethylene (80) sorbitan monooleate (CAS No. 9005-65-6), sorbitane monostearate (CAS No. 1338-41-6, available as Span™ 60 from Croda International PLC), polyoxyethylenglycerol-triricinoleat 35 (CAS No. 61791-12-6, available as Cremophor EL® from BASF). The amount of surfactant may vary. In some embodiments, the amount of any surfactant such as those listed above may be about 0.001 to about 5%, about 0.1% to about 2%, or about 0.1% to about 1%.

An ophthalmic composition provided herein may include one or more viscosity modifying agents, including the class of hydrogel polymers. Examples of viscosity modifying agents include, but are not limited to, carboxymethyl cellulose (CMC) and salts thereof, cellulose polymers such as hydroxypropyl methyl cellulose (HPMC), alkyl acrylate crosspolymers such as a acrylates/C10-30 alkyl acrylate crosspolymer (e.g. Pemulen™), polyvinylpyrrolidone (PVP), hyaluronic acid (HA) and salts thereof, hydroxyethyl cellulose (HEC), ethyl hydroxyethyl cellulose, hydroxypropyl cellulose, methyl cellulose, dextran 70, gelatin, glycerine, polyethylene glycols, polysorbate 80, propylene glycol, povidone, carbomers, polyvinyl alcohol, alginates, carrageenans, guar gum, karaya gum, agarose gum, locust bean gum, tragacanth gum and xanthan gum.

In some embodiments, the hydrogel polymer is selected from CMC and its salts, HPMC, PVP, HEC, HA and its salts, and mixtures thereof. In some embodiments, the hydrogel polymer is sodium CMC.

In some embodiments, the viscosity agent may be a combination of a hydrogel polymer and an alkyl acrylate crosspolymer, such as an acrylates/C10-30 alkyl acrylate crosspolymer. Pemulen™ TR-2 (Lubrizol Corporation, Wickliffe, Ohio) is a commercially available acrylates/C10-30 alkyl acrylate crosspolymer. In some embodiments, the amount of acrylates/C10-30 alkyl acrylate crosspolymer is about 0.5% to about 1.5%; or about 0.8% to about 1.2%; or about 0.9% to about 1.1%; or about 1.0%.

An ophthalmic composition provided herein may include one or more tonicity agents. The tonicity agent may vary, and may include any compound or substance useful for adjusting the tonicity of an ophthalmic liquid. Examples include, but are not limited to, salts, particularly sodium chloride, potassium chloride, magnesium chloride and calcium chloride; polyols and sugars such as glycerin (glycerol), propylene glycol, erythritol, mannitol, sorbitol and trehalose; amino acids such as carnitine (e.g., levocarnitine or L-carnitine) and betaine; or any other suitable ophthalmically acceptable tonicity adjustor. The amount of tonicity agent may vary depending upon whether an isotonic, hypertonic, or hypotonic liquid is desired. In some embodiments, the amount of a tonicity agent such as those listed above may be at least about 0.001% up to about 1%, about 2%, or about 5%. In some embodiments, the amount of each tonicity agent is about 0.125%, about 0.25%, about 0.4%, about 0.5%, about 0.6%, about 0.75%, about 1.0%, about 1.25%, about 1.5%, about 1.75%, or about 2.0%

In some embodiments, the tonicity agents used herein to provide substantially isotonic, or slightly hypotonic, ophthalmically acceptable compositions. In some embodiments the osmolarity of the composition is 150 to 450 mOsm/kg; 250 to 330 mOsm/kg; 270 to 310 mOsm/kg; or about 240 mOsm/kg.

An ophthalmic composition provided herein may include one or more chelating agents. The chelating agent may vary, and may include any compound or substance that is capable of chelating a metal. A useful chelating agent is edetate disodium (EDTA), although other chelating agents may also be used in place or in conjunction with it.

While it is routine for ophthalmic solutions to contain antimicrobial preservatives, the compositions provided herein do not contain such preservatives. Examples of such excluded preservatives include, but are not limited to, cationic preservatives such as quaternary ammonium compounds including benzalkonium chloride, polyquad, and the like; guanidine-based preservatives including PHMB, chlorhexidine, and the like; chlorobutanol; mercury preservatives such as thimerosal, phenylmercuric acetate and phenylmercuric nitrate; and oxidizing preservatives such as stabilized oxychloro complexes (e.g. Purite®).

Compositions provided herein may be aqueous solutions or emulsions, or some other acceptable liquid form. For an emulsion, one or more oils in addition to the omega-3 oils may be used to in the emulsion. Suitable oils include, but are not limited to anise oil, castor oil, clove oil, cassia oil, cinnamon oil, almond oil, corn oil, arachis oil, cottonseed oil, safflower oil, maize oil, linseed oil, rapeseed oil, soybean oil, olive oil, caraway oil, rosemary oil, peanut oil, peppermint oil, sunflower oil, eucalyptus oil, sesame oil, and the like. In certain embodiments, the addition oil is castor oil.

Specific omega-3 oils include, but are not limited to, botanical oils such as linseed (flaxseed or *linum usitatissimum*), chia (chia sage or *salvia hispanica*), kiwifruit (Chinese gooseberry or *actinidia chinensis*), perilla (shiso or *perilla frutescens*), lingonberry (cowberry or *vaccinium vitis-idaea*), *camelina* (gold-of-pleasure or *camelina sativa*), purslane (*portulaca* or *portulaca oleracea*) and black raspberry (*rubus occidentalis*); and oils from cold water fish such as cod liver oil, salmon oil, anchovy oil and tuna oil. In certain embodiments, the omega-3 oil is flaxseed oil.

TABLE 1

Exemplary omega-3 acids present in omega-3 oils

| Common name | Lipid name | Chemical name |
|---|---|---|
| Hexadecatrienoic acid (HTA) | 16:3 (n-3) | all-cis-7,10,13-hexadecatrienoic acid |
| α-Linolenic acid (ALA) | 18:3 (n-3) | all-cis-9,12,15-octadecatrienoic acid |
| Stearidonic acid (SDA) | 18:4 (n-3) | all-cis-6,9,12,15-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Heneicosapentaenoic acid (HPA) | 21:5 (n-3) | all-cis-6,9,12,15,18-heneicosapentaenoic acid |
| Docosapentaenoic acid (DPA), Clupanodonic acid | 22:5 (n-3) | all-cis-7,10,13,16,19-docosapentaenoic acid |
| Docosahexaenoic acid (DHA) | 22:6 (n-3) | all-cis-4,7,10,13,16,19-docosahexaenoic acid |
| Tetracosapentaenoic acid | 24:5 (n-3) | all-cis-9,12,15,18,21-tetracosapentaenoic acid |
| Tetracosahexaenoic acid (Nisinic acid) | 24:6 (n-3) | all-cis-6,9,12,15,18,21-tetracosahexaenoic acid |

Any of the compositions provided herein may include, as an "omega-3 oil" one of the omega-3 acids of Table 1 or mixtures thereof, either from synthetic sources or as isolated from a natural oil.

Table 2 provides examples of plant seed oils which may be used as source of omega-3 components. One or more of the oils provided in Table 2 may be used as the omega-3 oil source for the emulsion formulations.

TABLE 2

| Common name | Alternative name | Linnaean name | % ALA |
|---|---|---|---|
| Kiwifruit | Chinese gooseberry | *Actinidia deliciosa* | 63 |
| Perilla | shiso | *Perilla frutescens* | 61 |
| Chia seed | chia sage | *Salvia hispanica* | 58 |
| Flax | linseed | *Linum usitatissimum* | 53-59 |
| Lingonberry | Cowberry | *Vaccinium vitis-idaea* | 49 |
| Camelina | Gold-of-pleasure | *Camelina sativa* | 36 |
| Purslane | Portulaca | *Portulaca oleracea* | 35 |
| Black raspberry | | *Rubus occidentalis* | 33 |
| Hemp | | *Cannabis sativa* | 19 |
| Canola | | | 9-11 |

In specific embodiments, the ophthalmic compositions provided herein comprise one or more omega-3 oils, castor oil, BHT and/or BHA, one or more hydrogels, one or more tonicity agents, one or more surfactants, and an acrylates/C10-30 alkyl acrylate crosspolymer, and do not include an antimicrobial preservative.

In other embodiments, the ophthalmic compositions provided herein comprise flaxseed oil, castor oil, BHT and/or BHA, one or more hydrogels, one or more tonicity agents, one or more surfactants, and an acrylates/C10-30 alkyl acrylate crosspolymer, and do not include an antimicrobial preservative.

In one embodiment, provided herein is an ophthalmic composition comprising flaxseed oil, castor oil, BHT, one or more hydrogels, one or more tonicity agents, one or more surfactants, and an acrylates/C10-30 alkyl acrylate crosspolymer, and wherein the composition does not include an antimicrobial preservative.

In one embodiment, provided herein is an ophthalmic composition comprising flaxseed oil, castor oil, BHA, one or more hydrogels, one or more tonicity agents, one or more surfactants, and an acrylates/C10-30 alkyl acrylate crosspolymer, and wherein the composition does not include an antimicrobial preservative.

In one embodiment, provided herein is an ophthalmic composition comprising flaxseed oil, castor oil, BHT, BHA, one or more hydrogels, one or more tonicity agents, one or more surfactants, and an acrylates/C10-30 alkyl acrylate crosspolymer, and wherein the composition does not include an antimicrobial preservative.

In one embodiment, provided herein is an ophthalmic composition comprising flaxseed oil; castor oil; BHT and/or BHA; CMC or a salt thereof; one or more tonicity agents; one or more surfactants; and an acrylates/C10-30 alkyl acrylate crosspolymer; and wherein the composition does not include an antimicrobial preservative.

In one embodiment, provided herein is an ophthalmic composition comprising flaxseed oil; castor oil; BHT and/or BHA; CMC or a salt thereof; one or more tonicity agents selected from carnitine, glycerin, erythritol and trehalose; one or more surfactants; and an acrylates/C10-30 alkyl acrylate crosspolymer; and wherein the composition does not include an antimicrobial preservative.

In one embodiment, provided herein is an ophthalmic composition comprising flaxseed oil; castor oil; BHT and/or BHA; CMC or a salt thereof; one or more tonicity agents selected from carnitine, glycerin, erythritol and trehalose; one or more surfactants selected from polysorbate 80 and POE 40 stearate; and an acrylates/C10-30 alkyl acrylate crosspolymer; and wherein the composition does not include an antimicrobial preservative.

In one embodiment, provided herein is an ophthalmic composition comprising flaxseed oil; castor oil; BHT and/or BHA; sodium CMC; one or more tonicity agents selected from carnitine, glycerin, erythritol and trehalose; one or more surfactants selected from polysorbate 80 and POE 40 stearate; and an acrylates/C10-30 alkyl acrylate crosspolymer; and wherein the composition does not include an antimicrobial preservative.

In one embodiment, provided herein is an ophthalmic composition comprising flaxseed oil; castor oil; BHT and/or BHA; sodium CMC; one or more tonicity agents selected from carnitine, glycerin, erythritol and trehalose; polysorbate 80; POE 40 stearate; and an acrylates/C10-30 alkyl acrylate crosspolymer; and wherein the composition does not include an antimicrobial preservative.

In one embodiment, provided herein is an ophthalmic composition comprising flaxseed oil; castor oil; BHT and/or BHA; sodium CMC; carnitine; glycerin; erythritol; trehalose; a buffer; polysorbate 80; POE 40 stearate; and an acrylates/C10-30 alkyl acrylate crosspolymer; and wherein the composition does not include an antimicrobial preservative.

In one embodiment, provided herein is an ophthalmic composition comprising flaxseed oil; castor oil; BHT and/or BHA; sodium CMC; carnitine; glycerin; erythritol; trehalose; boric acid; polysorbate 80; POE 40 stearate; and an acrylates/C10-30 alkyl acrylate crosspolymer; and wherein the composition does not include an antimicrobial preservative.

In one embodiment, provided herein is an ophthalmic composition comprising flaxseed oil; castor oil; BHT; sodium CMC; carnitine; glycerin; erythritol; trehalose; boric acid; polysorbate 80; POE 40 stearate; an acrylates/C10-30 alkyl acrylate crosspolymer; and water; and wherein the composition does not include an antimicrobial preservative.

In one embodiment, provided herein is an ophthalmic composition comprising flaxseed oil; castor oil; BHT; BHA; sodium CMC; carnitine; glycerin; erythritol; trehalose; boric acid; polysorbate 80; POE 40 stearate; an acrylates/C10-30 alkyl acrylate crosspolymer; and water; and wherein the composition does not include an antimicrobial preservative.

When the term "about" is used herein, it is understood to encompass a reasonable range of variation around the value provided. A reasonable variation is understood by those skilled in the art to depend on the art and the specific circumstances of the defined value. In some embodiments, "about" includes a +/−30% variation from the value provided. In some embodiments, "about" includes a +/−25% variation from the value provided. In some embodiments, "about" includes a +/−10% variation from the value provided. In some embodiments, "about" includes a +/−5% variation from the value provided. In some embodiments, "about" includes a +/−1% variation from the value provided.

In one embodiment, provided herein is an ophthalmic composition comprising about 0.1% to about 1% w/w flaxseed oil; about 0.1% to about 1% w/w castor oil; about 0.001% to about 0.05% w/w BHT; about 0.001% to about 0.05% w/w BHA; about 0.25% to about 1% w/w sodium CMC; about 0.1% to about 0.5% w/w carnitine; about 0.1% to about 2% w/w glycerin; about 0.1% to about 0.5% w/w erythritol; about 0.5% to about 3% w/w trehalose; about 0.1% to about 2% w/w boric acid; about 0.1% to about 2% w/w polysorbate 80; about 0.1% to about 2% w/w POE 40 stearate; about 0.1% to about 1% w/w acrylates/C10-30 alkyl acrylate crosspolymer; and water; and wherein the composition does not include an antimicrobial preservative.

In one embodiment, provided herein is an ophthalmic composition comprising about 0.1% to about 1% w/w flaxseed oil; about 0.1% to about 1% w/w castor oil; about 0.001% to about 0.05% w/w BHT; about 0.25% to about 1% w/w sodium CMC; about 0.1% to about 0.5% w/w carnitine; about 0.1% to about 2% w/w glycerin; about 0.1% to about 0.5% w/w erythritol; about 0.5% to about 3% w/w trehalose; about 0.1% to about 2% w/w boric acid; about 0.1% to about 2% w/w polysorbate 80; about 0.1% to about 2% w/w POE 40 stearate; about 0.05% to about 1% w/w acrylates/C10-30 alkyl acrylate crosspolymer; and water; and wherein the composition does not include an antimicrobial preservative.

In one embodiment, provided herein is an ophthalmic composition comprising about 0.1% to about 0.5% w/w flaxseed oil; about 0.1% to about 0.5% w/w castor oil; about 0.005% to about 0.02% w/w BHT; about 0.005% to about 0.02% w/w BHA; about 0.25% to about 1% w/w sodium CMC; about 0.1% to about 0.5% w/w carnitine; about 0.5% to about 2% w/w glycerin; about 0.1% to about 0.5% w/w erythritol; about 1% to about 2% w/w trehalose; about 0.25% to about 1% w/w boric acid; about 0.25% to about 1% w/w polysorbate 80; about 0.1% to about 1% w/w POE 40 stearate; about 0.05% to about 0.25% w/w acrylates/C10-30 alkyl acrylate crosspolymer; and water; and wherein the composition does not include an antimicrobial preservative.

In one embodiment, provided herein is an ophthalmic composition comprising about 0.1% to about 0.5% w/w flaxseed oil; about 0.1% to about 0.5% w/w castor oil; about 0.005% to about 0.02% w/w BHT; about 0.25% to about 1% w/w sodium CMC; about 0.1% to about 0.5% w/w carnitine; about 0.5% to about 2% w/w glycerin; about 0.1% to about 0.5% w/w erythritol; about 1% to about 2% w/w trehalose; about 0.25% to about 1% w/w boric acid; about 0.25% to about 1% w/w polysorbate 80; about 0.1% to about 1% w/w POE 40 stearate; about 0.05% to about 0.25% w/w acrylates/C10-30 alkyl acrylate crosspolymer; and water; and wherein the composition does not include an antimicrobial preservative.

In one embodiment, provided herein is an ophthalmic composition comprising about 0.1% to about 0.25% w/w flaxseed oil; about 0.1% to about 0.25% w/w castor oil; about 0.005% to about 0.02% w/w BHT; about 0.005% to about 0.02% w/w BHA; about 0.25% to about 1% w/w sodium CMC; about 0.1% to about 0.5% w/w carnitine; about 0.5% to about 2% w/w glycerin; about 0.1% to about 0.5% w/w erythritol; about 1% to about 2% w/w trehalose; about 0.25% to about 1% w/w boric acid; about 0.25% to about 1% w/w polysorbate 80; about 0.1% to about 1% w/w POE 40 stearate; about 0.05% to about 0.25% w/w acrylates/C10-30 alkyl acrylate crosspolymer; and water; and wherein the composition does not include an antimicrobial preservative.

In one embodiment, provided herein is an ophthalmic composition comprising about 0.1% to about 0.25% w/w flaxseed oil; about 0.1% to about 0.25% w/w castor oil; about 0.02% w/w BHT; about 0.25% to about 1% w/w sodium CMC; about 0.1% to about 0.5% w/w carnitine; about 0.5% to about 2% w/w glycerin; about 0.1% to about 0.5% w/w erythritol; about 1% to about 2% w/w trehalose; about 0.25% to about 1% w/w boric acid; about 0.25% to about 1% w/w polysorbate 80; about 0.1% to about 1% w/w POE 40 stearate; about 0.05% to about 0.25% w/w acrylates/C10-30 alkyl acrylate crosspolymer; and water; and wherein the composition does not include an antimicrobial preservative.

In one embodiment, provided herein is an ophthalmic composition consisting essentially of about 0.125% w/w flaxseed oil; about 0.125% w/w castor oil; about 0.005% to about 0.02% w/w BHT; about 0.005% to about 0.02% w/w BHA; about 0.5% w/w sodium CMC; about 0.25% w/w carnitine; about 1% w/w glycerin; about 0.25% w/w erythritol; about 1.5% w/w trehalose; about 0.6% w/w boric acid; about 0.5% w/w polysorbate 80; about 0.25% to about 0.5% w/w POE 40 stearate; about 0.1% w/w acrylates/C10-30 alkyl acrylate crosspolymer; and water; and wherein the composition does not include an antimicrobial preservative.

In one embodiment, provided herein is an ophthalmic composition consisting essentially of about 0.125% w/w flaxseed oil; about 0.125% w/w castor oil; about 0.02% w/w BHT; about 0.5% w/w sodium CMC; about 0.25% w/w carnitine; about 1% w/w glycerin; about 0.25% w/w erythritol; about 1.5% w/w trehalose; about 0.6% w/w boric acid; about 0.5% w/w polysorbate 80; about 0.25% to about 0.5% w/w POE 40 stearate; about 0.1% w/w acrylates/C10-30 alkyl acrylate crosspolymer; and water; and wherein the composition does not include an antimicrobial preservative.

In other embodiments, the ophthalmic composition comprises, consists essentially of, or consists of the specific exemplary emulsions provided in Tables 3-10 below. In each instance, the weight percentage may be approximate, meaning that each ingredient is present in about the weight percentage specified (i.e., the weight percentage may vary by the amounts as defined by "about" herein). In other embodiments, the weight percentage provided is exactly that provided.

Specific compositions containing flaxseed oil (a.k.a., linseed oil) as the source of omega-3 fatty acids are listed in Table 3. These compositions were found to exhibit excellent chemical and physical stability. Other compositions with good chemical/physical stability are provided in the examples that follow.

TABLE 3

| Formulation ID Components | Formulation 1 % w/w | Formulation 2 % w/w | Formulation 3 % w/w |
| --- | --- | --- | --- |
| Glycerin | 1 | 1 | 1 |
| Sodium CMC | 0.5 | 0.5 | 0.5 |
| Polysorbate 80 | 0.5 | 0.5 | 0.5 |
| Flaxseed Oil | 0.125 | 0.25 | 0.125 |
| Castor Oil | 0.125 | 0.25 | 0.125 |
| POE 40 Stearate | 0.25 | 0.5 | 0.25 |
| BHA | — | 0.02 | 0.005 |
| BHT | 0.02 | 0.02 | 0.005 |
| Pemulen | 0.1 | 0.1 | 0.1 |
| L-Carnitine | 0.25 | 0.25 | 0.25 |
| Erythritol | 0.25 | 0.25 | 0.25 |
| Trehalose | 1.5 | 1.5 | 1.5 |
| Boric Acid | 0.6 | 0.6 | 0.6 |
| Water | qs to 100 | qs to 100 | qs to 100 |

EXAMPLES

The following non-limiting examples are made for illustrative purposes. Each example represents at least one embodiment provided herein.

Example 1

The addition of BHA and BHT in the oil phase of an emulsion designated as "Formulation 5" improves the chemical stability of omega-3 oils in said emulsions as compared to "Formulation 4" which contains no BHA or BHT. See FIG. 1. Degradation of omega-3 oil is observed within two months in emulsions not containing BHA and BHT (OmE-B) stored at both room temperature and 40° C., while those containing BHA and BHT (OmE-C) are stable at all 3 temperatures during this period. The composition of Formulation 4 and Formulation 5 is provided in Table 4 below.

TABLE 4

| | (% w/w) | |
| --- | --- | --- |
| Ingredient | Form. 4 | Form. 5 |
| Flaxseed Oil | 1.000 | 1.000 |
| Castor Oil | | |
| Polysorbate 80 | | |
| Solutol | 1.000 | 1.000 |
| BHA | | 0.100 |
| BHT | | 0.100 |
| Alpha-Tocopherol | | |
| Vit E Acetate | 0.500 | |
| Captisol (SB-CD) | 1.000 | |
| Glycerin | 1.000 | 1.000 |
| Pemulen | 0.100 | 0.100 |
| Boric acid | 0.600 | 0.600 |
| Water | QS | QS |
| pH Adjustment | 6.4-7.2 | 6.4-7.2 |

Example 2

Addition of BHA and BHT in the oil phase improved physical stability to omega-3 oils in emulsion. Formulation 6 containing only BHA/BHT in oil phase maintained its white opaque appearance at all storage conditions (5° C., 25° C. and 40° C.) over 3 months, while discoloration seen for emulsions containing α-tocopherol and ascorbyl palmitate over the same duration (Formulations 7 and 8). Discoloration was found to be due to chemical degradation of omega-3 fatty acids. Data shown is for samples stored at 40° C. for 3 months.

TABLE 5

| | % w/w | | |
| --- | --- | --- | --- |
| | Formulation 6 | Formulation 7 | Formulation 8 |
| Flaxseed Oil | 0.5 | 1 | 0.5 |
| Castor Oil | 0.5 | | 0.5 |
| Solutol | 0.5 | 1 | 0.5 |
| POE 40 Stearate | 0.5 | | 0.5 |
| Alpha-Tocopherol | | 0.05 | 0.05 |
| Ascorbyl Palmitate | | | 0.1 |
| BHA | 0.02 | 0.02 | 0.02 |
| BHT | 0.02 | 0.02 | 0.02 |
| EDTA | 0.05 | | |
| Pyruvate | 0.1 | | |
| Trehalose | 3 | | |
| Glycerin | 0.5 | 1 | 1 |
| Pemulen | 0.1 | 0.1 | 0.1 |
| Boric acid | 0.6 | 0.6 | 0.6 |
| Water | qs | qs | qs |
| Adjust pH to (Target PH = 7) | 6.4-7.2 | 6.4-7.2 | 6.4-7.2 |

Example 3

Figure 2:
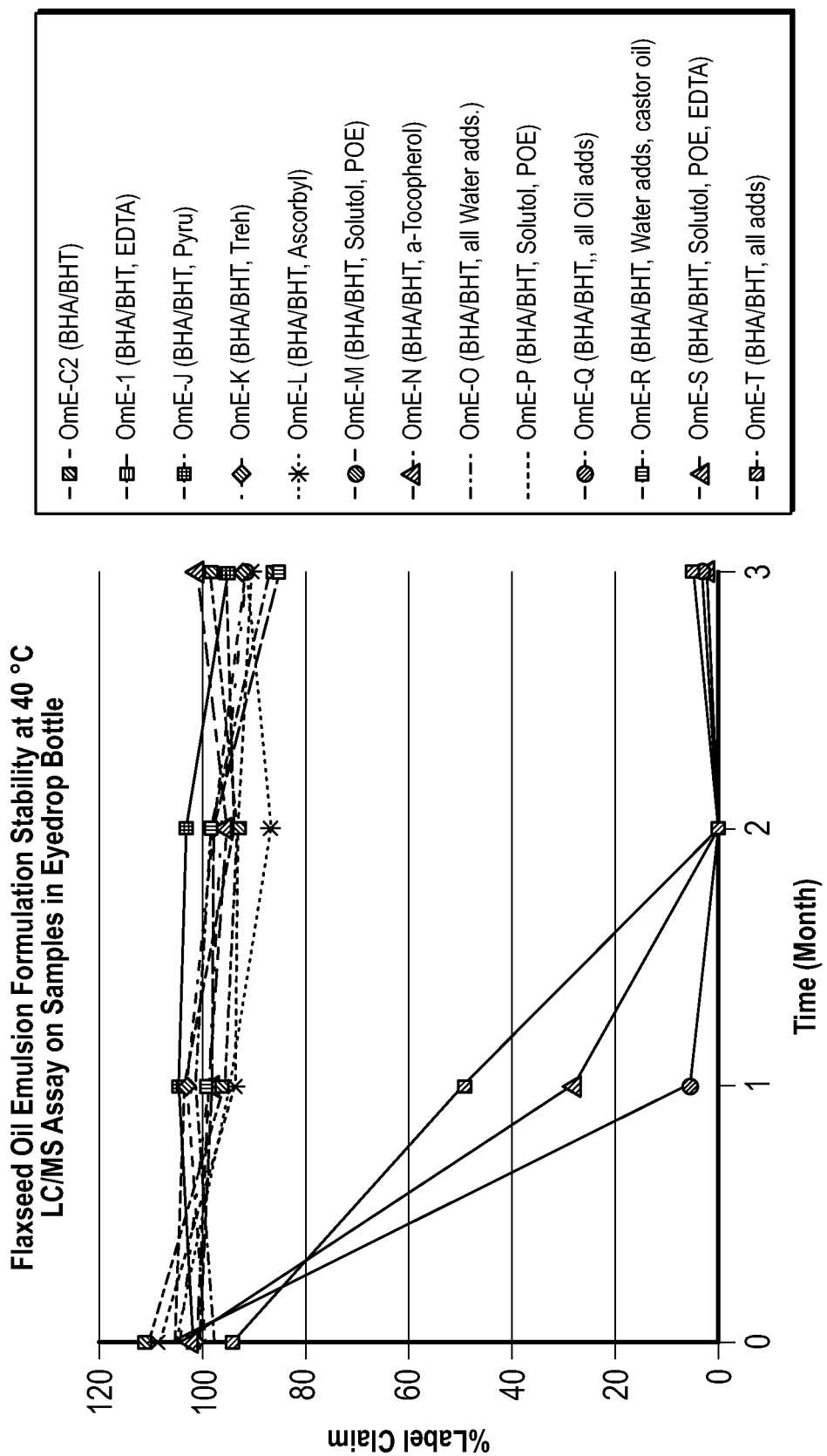
FIG. 2 shows flaxseed oil emulsion formulation stability over time.

Inclusion of excipients which are reported in literature as oil soluble antioxidants, such as alpha-tocopherol and vitamin-E-acetate, surprisingly worsened the chemical stability of omega-3 oils in emulsion. See FIG. 2. No significant impact of water soluble additives such as pyruvate or EDTA to the stability of omega-3 oils was observed. The composition of each of the tested emulsions is provided in Table 10 at the end of these examples.

Example 4

Formulation compositions were optimized to select ingredients to provide maximum stability for the omega-3 emulsion compositions. Compositions of two exemplary lead formulations (Formulation 1 and Formulation 3) are shown in Table 6 below.

TABLE 6

| Test | Flaxseed Oil (% linolenic oil) | | | | | | |
|---|---|---|---|---|---|---|---|
| Timepoint | 0 | 1 month | | 2 months | | 3 months | |
| Condition | 25° C. | 25° C. | 40° C. | 25° C. | 40° C. | 25° C. | 40° C. |
| Formulation 1 | 100.2 | 110.6 | 109.9 | 101.41 | 89.00 | 99.06 | 89.86 |
| Formulation 3 | 98.0 | 106.3 | 108.9 | 90.17 | 89.33 | 102.82 | 98.42 |

Table 6 shows the chemical & physical stability of the exemplary formulations. Flaxseed oil analysis was done by LCMS by quantification of the triglyceride of linolenic acid (omega-3 component). No significant degradation of the triglyceride of linolenic acid was observed and all results were within analytical error for the method (±10%). Formulations 1 and 3 each remained white/translucent in color with no discoloration, creaming or oil separation after storage for 5 months at 25° C. and 40° C. See Table 6.

Example 5

Globule size analysis of each of Formulation 1 and Formulation 3 was performed to further evaluate the stability of the omega-3 component. See Table 7 below. No changes in globule size of the emulsions was observed over the course of three months of stability monitoring. These results further confirm the stability of emulsions Formulations 1 and 3, and other similar omega-3 emulsions containing BHT and/or BHA.

TABLE 7

| Time-point | | Globule Size (μm) | | | | | | |
|---|---|---|---|---|---|---|---|---|
| | | 0 | 1 month | | 2 months | | 3 months | |
| Condition | | 25° C. | 25° C. | 40° C. | 25° C. | 40° C. | 25° C. | 40° C. |
| Form. 1 | D10 | 0.2039 | N/A | 0.3096 | 0.2184 | 0.2174 | 0.4025 | 0.1978 |
| | D50 | 0.2744 | N/A | 0.4344 | 0.2931 | 0.2921 | 0.5579 | 0.2710 |
| | D90 | 0.3634 | N/A | 0.5920 | 0.3851 | 0.3843 | 0.7613 | 0.3656 |
| Form. 3 | D10 | 0.2138 | 0.2293 | 0.2362 | 0.2144 | 0.2455 | 0.4066 | 0.2282 |
| | D50 | 0.2877 | 0.3076 | 0.3197 | 0.2890 | 0.3305 | 0.5593 | 0.3056 |
| | D90 | 0.3796 | 0.4084 | 0.4240 | 0.3818 | 0.4367 | 0.7537 | 0.4052 |

Example 6 pH and osmolality analysis was performed to further evaluate the stability of the omega-3 components in the test formulations. See Table 8 below. The test formulations showed no changes over 3 months of stability monitoring, demonstrating chemical and physical stability of the omega-3 emulsions.

Tolerability of the test emulsions were evaluated in a rabbit model. Formulations 1 and 3 were found to be well-tolerated. See FIG. 3. While each was well-tolerated, Formulation 1 demonstrated the lowest discomfort score in vivo, showing that the emulsion was particularly well-tolerated.

TABLE 8

| Test | pH | | | | | | |
|---|---|---|---|---|---|---|---|
| Timepoint | 0 | 1 month | | 2 months | | 3 months | |
| Condition | 25° C. | 25° C. | 40° C. | 25° C. | 40° C. | 25° C. | 40° C. |
| Form. 1 | 7.23 | 7.25 | 7.24 | 7.11 | 7.14 | 7.23 | 7.22 |
| Form. 3 | 7.17 | 7.13 | 7.12 | 7.03 | 7.04 | 7.12 | 7.12 |
| Test | Osmolality (mOsm/kg) | | | | | | |
| Timepoint | 0 | 1 month | | 2 months | | 3 months | |
| Condition | 25° C. | 25° C. | 40° C. | 25° C. | 40° C. | 25° C. | 40° C. |
| Form. 1 | 305 | 306 | 308 | 319 | 323 | 294 | 298 |
| Form. 3 | 306 | 306 | 307 | 318 | 324 | 298 | 300 |

TABLE 9

| Formulation # | 8 | 9 | 10 | 11 | 12 | 13 | 14 | 15 |
|---|---|---|---|---|---|---|---|---|
| Ingredients (% w/w) | | | | | | | | |
| Glycerin | 1 | 1 | 1 | 1 | 1 | 1 | 1 | 1 |
| Sodium CMC | 0.5 | 0.5 | 0.5 | 0.5 | 0.5 | 0.5 | 0.5 | 0.5 |
| Flaxseed Oil | 0.125 | 0.125 | 0.25 | 0.125 | 0.125 | 0.125 | 0.125 | 0.125 |
| Castor Oil | 0.125 | 0.125 | 0.25 | 0.125 | 0.125 | 0.125 | 0.125 | 0.125 |
| Solutol | — | — | 0.25 | — | — | — | — | — |
| POE 40 Stearate | — | 0.25 | 0.5 | 0.25 | 0.25 | 0.25 | 0.25 | — |
| Polysorbate 80 | 0.5 | 0.5 | 0.5 | — | 0.5 | 0.5 | 0.25 | 0.5 |
| BHA | 0.02 | 0.02 | 0.02 | 0.02 | — | 0.005 | 0.02 | 0.02 |
| BHT | 0.02 | 0.02 | 0.02 | 0.02 | 0.02 | 0.005 | 0.02 | 0.02 |
| Pemulen | 0.1 | 0.1 | 0.1 | 0.1 | 0.1 | 0.1 | 0.1 | 0.1 |
| L-Carnitine | 0.25 | 0.25 | 0.25 | 0.25 | 0.25 | 0.25 | 0.25 | 0.25 |
| Elythritol | 0.25 | 0.25 | 0.25 | 0.25 | 0.25 | 0.25 | 0.5 | 0.5 |
| Trehalose | 1.5 | 1.5 | 1.5 | 1.5 | 1.5 | 1.5 | — | — |
| Boric Acid | 0.6 | 0.6 | 0.6 | 0.6 | 0.6 | 0.6 | 0.6 | 0.6 |
| Water | qs | qs | qs | qs | qs | qs | qs | qs |

TABLE 10a

| Formulation # | 16 | 17 | 18 | 19 | 20 | 21 | 22 |
|---|---|---|---|---|---|---|---|
| Ingredients (% w/w) | | | | | | | |
| Study factor | ↓BHA/BHT in OmE-C | ↓BHA/BHT + EDTA in OmE-C | ↓BHA/BHT + Pyruvate in OmE-C | ↓BHA/BHT + Trehalose in OmE-C | ↓BHA/BHT + Ascorbyl in OmE-C | Solutol + POE in OmE-C | Alpha Tocopherol in OmE-C |
| Flaxseed Oil | 1.0 | 1.0 | 1.0 | 1.0 | 1.0 | 1.0 | 1.0 |
| Castor Oil | | | | | | | |
| Solutol | 1.0 | 1.0 | 1.0 | 1.0 | 1.0 | 0.5 | 1.0 |
| POE 40 Stearate | | | | | | 0.5 | |
| Alpha-Tocopherol | | | | | | | 0.05 |
| Ascorbyl Palmitate | | | | | 0.1 | | |
| BHA | 0.02 | 0.02 | 0.02 | 0.02 | 0.02 | 0.02 | 0.02 |
| BHT | 0.02 | 0.02 | 0.02 | 0.02 | 0.02 | 0.02 | 0.02 |
| EDTA | | 0.05 | | | | | |
| Pyruvate | | | 0.1 | | | | |
| Trehalose | | | | 3.0 | | | |
| Glycerin | 1.0 | 1.0 | 1.0 | 0.5 | 1.0 | 1.0 | 1.0 |
| Pemulen | 0.1 | 0.1 | 0.1 | 0.1 | 0.1 | 0.1 | 0.1 |
| Boric acid | 0.6 | 0.6 | 0.6 | 0.6 | 0.6 | 0.6 | 0.6 |
| Water | qs | qs | qs | qs | qs | qs | qs |
| Adjust pH to | 6.4-7.2 | 6.4-7.2 | 6.4-7.2 | 6.4-7.2 | 6.4-7.2 | 6.4-7.2 | 6.4-7.2 |

TABLE 10b

| Formulation # | 22 | 23 | 24 | 25 | Form. 6 | 26 | 27 |
|---|---|---|---|---|---|---|---|
| Ingredients (% w/w) | | | | | | | |
| Study factor | Alpha Tocopherol in OmE-C | Water Antioxidants in OmE-C | ↓BHA/BHT + Solutol + POE 40 in OmE-C | Oil soluble Antioxidants in OmE-G | Water Antioxi + Solutol + POE 40 in OmE-G | ↓BHA/BHT + EDTA in OmE-G | All Antioxidants in OmE-G |
| Flaxseed Oil | 1.0 | 1.0 | 0.5 | 0.5 | 0.5 | 0.5 | 0.5 |
| Castor Oil | | | 0.5 | 0.5 | 0.5 | 0.5 | 0.5 |
| Solutol | 1.0 | 1.0 | 0.5 | 0.5 | 0.5 | 0.5 | 0.5 |
| POE 40 Stearate | | | 0.5 | 0.5 | 0.5 | 0.5 | 0.5 |
| Alpha-Tocopherol | 0.05 | | | 0.05 | | | 0.05 |
| Ascorbyl Palmitate | | | | 0.1 | | | 0.1 |
| BHA | 0.02 | 0.02 | 0.02 | 0.02 | 0.02 | 0.02 | 0.02 |

TABLE 10b-continued

| Formulation # | 22 | 23 | 24 | 25 | Form. 6 | 26 | 27 |
|---|---|---|---|---|---|---|---|
| | | | Ingredients (% w/w) | | | | |
| Study factor | Alpha Tocopherol in OmE-C | Water Antioxidants in OmE-C | ↓BHA/BHT + Solutol + POE 40 in OmE-G | Oil soluble Antioxidants in OmE-G | Water Antioxi + Solutol + POE 40 in OmE-G | ↓BHA/BHT + EDTA in OmE-G | All Antioxidants in OmE-G |
| BHT | 0.02 | 0.02 | 0.02 | 0.02 | 0.02 | 0.02 | 0.02 |
| EDTA | | 0.05 | | | 0.05 | 0.05 | 0.05 |
| Pyruvate | | 0.1 | | | 0.1 | | 0.1 |
| Trehalose | | 3.0 | | | 3.0 | | 3.0 |
| Glycerin | 1.0 | 0.5 | 1.0 | 1.0 | 0.5 | 1.0 | 0.5 |
| Pemulen | 0.1 | 0.1 | 0.1 | 0.1 | 0.1 | 0.1 | 0.1 |
| Boric acid | 0.6 | 0.6 | 0.6 | 0.6 | 0.6 | 0.6 | 0.6 |
| Water | qs | qs | qs | qs | qs | qs | qs |
| Adjust pH to | 6.4-7.2 | 6.4-7.2 | 6.4-7.2 | 6.4-7.2 | 6.4-7.2 | 6.4-7.2 | 6.4-7.2 |

Methods of Treatment

Provided herein are methods for the diagnosis, treatment, or prevention of keratoconjunctivitis or dry eye syndrome. The methods of diagnosis, treatment, or prevention described herein may be performed by the topical application of a composition provided herein directly to the eye or the surround tissue of the eye.

Abnormalities of the tear film include an absolute or partial deficiency in aqueous tear production is known as keratoconjunctivitis sicca, or KCS. Keratoconjunctivitis sicca is typically caused by inadequate tear production. The aqueous tear layer is affected, resulting in aqueous tear deficiency or lacrimal hyposecretion. The lacrimal gland does not produce sufficient tears to keep the entire conjunctiva and cornea covered by a complete layer. This usually occurs in people who are otherwise healthy. Increased age is associated with decreased tearing. This is the most common type found in postmenopausal women. Causes include idiopathic, congenital alacrima, xerophthalmia, lacrimal gland ablation, and sensory denervation. In rare cases, it may be a symptom of collagen vascular diseases, including rheumatoid arthritis, Wegener's granulomatosis, and systemic lupus erythematosus.

In relatively mild cases, the main symptom of keratoconjunctivitis sicca is a foreign body sensation or a mild scratchiness. This can progress to become a constant, intense burning or irritative sensation that can be debilitating to a patient. More severe forms can progress to the development of filamentary keratitis, a painful condition characterized by the appearance of numerous strands or filaments attached to the corneal surface. Evidence suggests that these filaments represent breaks in the continuity of normal corneal epithelial cells. The shear created by lid motion pulls these filaments, causing pain. Management of this stage of keratoconjunctivitis sicca is very difficult.

A frequent complication of keratoconjunctivitis sicca is secondary infection. Several breakdowns in the eye's normal defense mechanisms seem to occur, presumably attributable to a decrease in the concentration of antibacterial lysozyme in the aqueous tears of a patient suffering from keratoconjunctivitis sicca.

Although keratoconjunctivitis sicca can develop in the absence of any other overt system abnormality, there is a frequent association of keratoconjunctivitis sicca with systemic disease. Keratoconjunctivitis sicca can occur as part of a larger systemic involvement known as Sjogren's syndrome. This classically consists of dry eyes, dry mouth and arthritis. Sjogren's syndrome and autoimmune diseases associated with Sjogren's syndrome are also conditions associated with aqueous tear deficiency. Drugs such as isotretinoin, sedatives, diuretics, tricyclic antidepressants, antihypertensives, oral contraceptives, antihistamines, nasal decongestants, beta-blockers, phenothiazines, atropine, and pain relieving opiates such as morphine can cause or worsen this condition. Infiltration of the lacrimal glands by sarcoidosis or tumors, or postradiation fibrosis of the lacrimal glands can also cause this condition. Histologically, in keratoconjunctivitis sicca (as part of Sjogren's syndrome or in isolation), the initial changes seen in the lacrimal glands are those of focal lymphocytic and plasma cell infiltrates associated with degeneration of glandular tissue. These changes resemble those seen in autoimmune disease in other tissue, giving rise to the speculation that keratoconjunctivitis sicca has an autoimmune basis.

Keratoconjunctivitis sicca can also be caused by abnormal tear composition resulting in rapid evaporation or premature destruction of the tears. When caused by rapid evaporation, it is termed evaporative dry eyes. In this condition, although the tear gland produces a sufficient amount of tears, the rate of evaporation of the tears is too rapid. There is a loss of water from the tears that results in tears that are too "salty" or hypertonic. As a result, the entire conjunctiva and cornea cannot be kept covered with a complete layer of tears during certain activities or in certain environments.

In general, dry eye symptoms may be caused by aging as tear production tends to decrease with age. Dry eye may also be caused by injury to the eye, burns, diabetes, or by adenoviruses. Dry eye may also be caused by contact lens use or by ocular surgical procedures.

Therefore, in some embodiments, provided herein are methods for the treatment of keratoconjunctivitis sicca or dry eye syndrome in a human or other mammal, with or without therapeutic agents, as caused by any one or more of the above factors or other factors, using the ophthalmic compositions described herein. In some embodiments, provided herein are methods for the treatment of keratoconjunctivitis sicca or dry eye syndrome in a human or other mammal, with or without therapeutic agents, as caused by any one or more of the above factors or other factors, by topical application of the ophthalmic compositions described herein.

As provided herein, the term "treatment" as used herein refers to an approach (e.g., a procedure or regimen) for obtaining beneficial or desired results, including clinical results. "Treating" a disease, disorder or condition means that the extent, undesirable clinical manifestations, or both, of a disease, disorder or condition are lessened and/or the time course of the progression is slowed (i.e., lengthened in time), as compared to not treating the disease, disorder or condition. For purposes of the methods disclosed herein, beneficial or desired clinical results include, but are not limited to, alleviation or amelioration of one or more symptoms (e.g., symptoms of dry eye syndrome), diminishment of extent of disorder, stabilized (i.e., not worsening) state of disorder, delay or slowing of disorder progression, amelioration or palliation of the disorder, and remission (whether partial or total), whether detectable or undetectable.

As provided herein, the terms "effective amount," "therapeutically effective amount" and the like in the context of compositions and methods disclosed herein refer in the customary sense to an amount which is sufficient to bring about a desired result. Accordingly, a therapeutically effective amount employed in a treatment is a sufficient amount to reduce the extent, undesirable clinical manifestation, of both, of a disease, disorder or condition.

LASIK (laser in situ keratomileusis) and other vision correction procedures can cause dry eyes after they penetrate the eye's surface and reduce corneal nerve sensitivity. In some cases, the eye then fails to sense the need for lubrication and inadequate tear production results. Therefore, provided herein are methods of treating dry eye incident to or induced by ocular surgery. Ocular surgery includes, but is not limited to LASIK, small incision lenticule extraction (SMILE) procedures, and cataract procedures. See *Ocul. Surf.*, 8: 135-145 (2010); *Ophthamology*, 107: 2131-2135 (2000).

In one embodiment, the method of treatment ameliorates the symptoms of post-LASIK tear dysfunction. In another embodiment, the method of treatment ameliorates the symptoms of post-cataract surgery tear dysfunction. In another embodiment, the method of treatment ameliorates the symptoms of post-SMILE surgery tear dysfunction.

The terms "a," "an," "the" and similar referents used herein (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. An ophthalmic composition for the treatment of dry eye wherein the composition is an emulsion comprising about 1% w/w glycerin, about 0.5% w/w sodium carboxymethyl cellulose, about 0.5% w/w polysorbate 80, about 0.125% w/w flaxseed oil, about 0.125% w/w castor oil, about 0.25% w/w POE 40 Stearate, about 0.02% w/w BHT, about 0.1% w/w pemulen, about 0.25% w/w L-Carnitine, about 0.25% w/w erythritol, about 1.5% w/w trehalose, about 0.6% w/w boric acid and water; and wherein the ophthalmic composition does not include an antimicrobial preservative.

2. The ophthalmic composition of claim 1, wherein the composition does not include BHA.

3. The ophthalmic composition of claim 1, comprising 1% w/w glycerin, 0.5% w/w sodium carboxymethyl cellulose, 0.5% w/w polysorbate 80, 0.125% w/w flaxseed oil, 0.125% w/w castor oil, 0.25% w/w POE 40 Stearate, 0.02% w/w BHT, 0.1% w/w pemulen, 0.25% w/w L-Carnitine, 0.25% w/w erythritol, 1.5% w/w trehalose, 0.6% w/w boric acid and water.

4. The ophthalmic composition of claim 1, wherein the composition consists of about 1% w/w glycerin, about 0.5% w/w sodium carboxymethyl cellulose, about 0.5% w/w polysorbate 80, about 0.125% w/w flaxseed oil, about 0.125% w/w castor oil, about 0.25% w/w POE 40 Stearate, about 0.02% w/w BHT, about 0.1% w/w pemulen, about 0.25% w/w L-Carnitine, about 0.25% w/w erythritol, about 1.5% w/w trehalose, about 0.6% w/w boric acid and water.

5. The ophthalmic composition of claim 4, wherein the composition consists of 1% w/w glycerin, 0.5% w/w sodium carboxymethyl cellulose, 0.5% w/w polysorbate 80, 0.125% w/w flaxseed oil, 0.125% w/w castor oil, 0.25% w/w POE 40 Stearate, 0.02% w/w BHT, 0.1% w/w pemulen, 0.25% w/w L-Carnitine, 0.25% w/w erythritol, 1.5% w/w trehalose, 0.6% w/w boric acid and water.

6. An ophthalmic emulsion composition comprising about 0.1% to about 1% w/w flaxseed oil; about 0.1% to about 1% w/w castor oil; about 0.001% to about 0.05% w/w BHT; about 0.25% to about 1% w/w sodium CMC; about 0.1% to about 0.5% w/w carnitine; about 0.1% to about 2% w/w glycerin; about 0.1% to about 0.5% w/w erythritol; about 0.5% to about 3% w/w trehalose; about 0.1% to about 2% w/w boric acid; about 0.1% to about 2% w/w polysorbate 80; about 0.1% to about 2% w/w POE 40 stearate; about 0.05% to about 1% w/w acrylates/C10-30 alkyl acrylate crosspolymer; and water; and wherein the composition does not include an antimicrobial preservative.

7. An ophthalmic emulsion composition comprising about 0.1% to about 1% w/w flaxseed oil; about 0.1% to about 1% w/w castor oil; about 0.001% to about 0.05% w/w BHT; about 0.001% to about 0.05% w/w BHA; about 0.25% to about 1% w/w sodium CMC; about 0.1% to about 0.5% w/w carnitine; about 0.1% to about 2% w/w glycerin; about 0.1% to about 0.5% w/w erythritol; about 0.5% to about 3% w/w trehalose; about 0.1% to about 2% w/w boric acid; about 0.1% to about 2% w/w polysorbate 80; about 0.1% to about 2% w/w POE 40 stearate; about 0.1% to about 1% w/w acrylates/C10-30 alkyl acrylate crosspolymer; and water; and wherein the composition does not include an antimicrobial preservative.

8. A method of treating keratoconjunctivitis sicca or dry eye syndrome in a human or other mammal, the method comprising administering an effective amount of an ophthalmic composition according to any one of claims 1-5, 6, 7 to said human or other mammal.

* * * * *

UNITED STATES PATENT AND TRADEMARK OFFICE
CERTIFICATE OF CORRECTION

| | | Page 1 of 1 |
|---|---|---|
| PATENT NO. | : 10,279,005 B2 | |
| APPLICATION NO. | : 14/949352 | |
| DATED | : May 7, 2019 | |
| INVENTOR(S) | : Anuradha V. Gore et al. | |

It is certified that error appears in the above-identified patent and that said Letters Patent is hereby corrected as shown below:

In the Drawings

Figure 3:
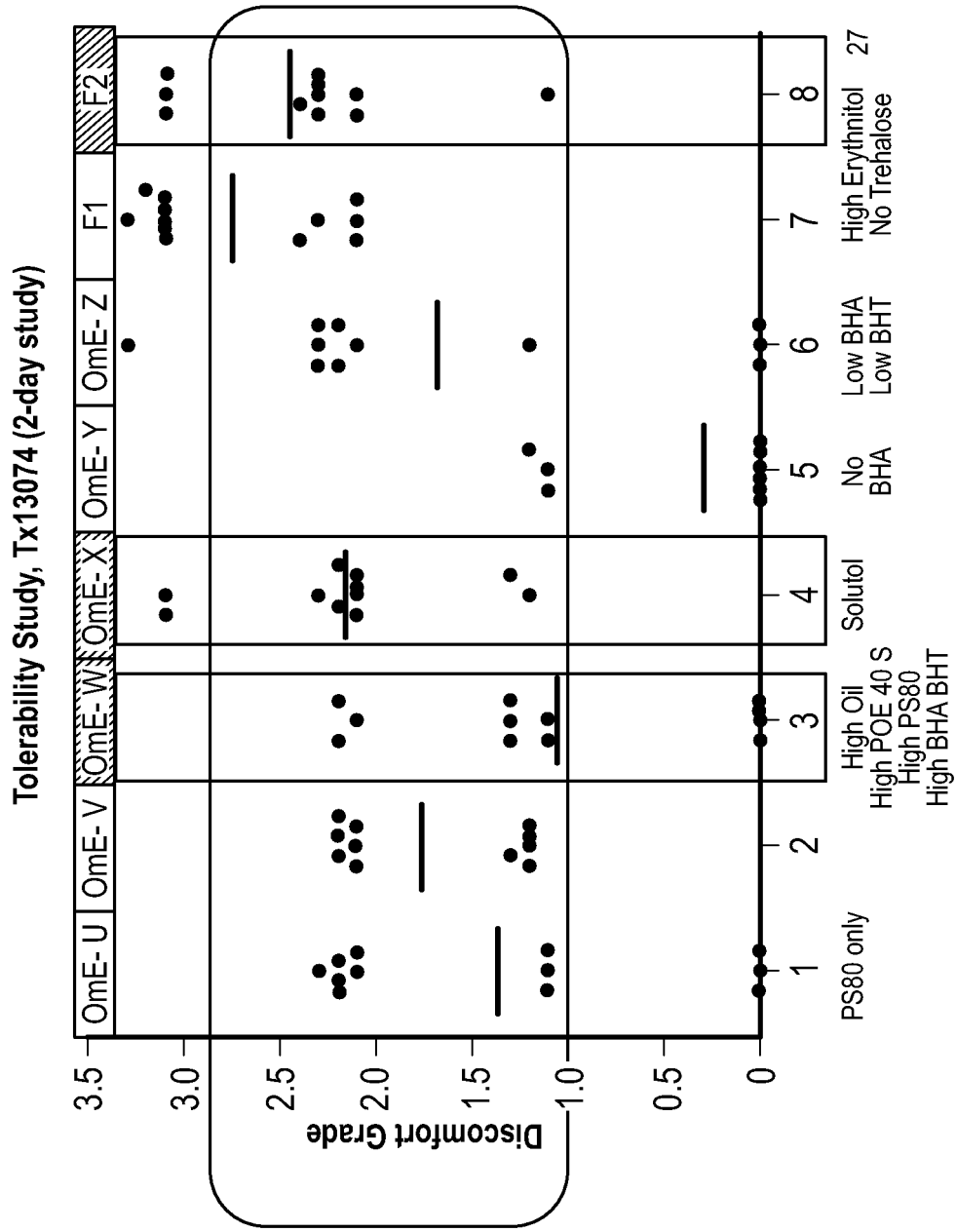
FIG. 3 shows in vivo tolerability results of omega-3 oil emulsions.

On sheet 3 of 3, in Figure 3, reference numeral 27, Line 1, delete "Erythnitol" and insert -- Erythritol --, therefor.

In the Specification

In Column 3, Line 51, delete "sorbitane" and insert -- sorbitan --, therefor.

In Column 4, Line 38, delete "2.0%" and insert -- 2.0%. --, therefor.

In Column 13, Line 15, delete "Elythritol" and insert -- Erythritol --, therefor.

In Column 17, Line 30, delete "Ophthamology," and insert -- Ophthalmology, --, therefor.

In the Claims

In Column 19, Lines 4-5, in Claim 8, delete "6, 7" and insert -- 6, or 7 --, therefor.

Signed and Sealed this
Sixteenth Day of July, 2019

Andrei Iancu
*Director of the United States Patent and Trademark Office*